United States Patent
Shimidzu et al.

(10) Patent No.: US 6,643,013 B1
(45) Date of Patent: Nov. 4, 2003

(54) GLOW DISCHARGE EMISSION SPECTROSCOPIC ANALYSIS APPARATUS

(75) Inventors: Ryosuke Shimidzu, Tokyo (JP); Thomas Nelis, Paris (FR); Susumu Matsumoto, Tokyo (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 09/376,164

(22) Filed: Aug. 17, 1999

(30) Foreign Application Priority Data

Dec. 22, 1998 (JP) .......................................... 10-365229

(51) Int. Cl.[7] .............................................. G01J 3/443
(52) U.S. Cl. ........................................................ 356/311
(58) Field of Search ........................................ 356/311

(56) References Cited

U.S. PATENT DOCUMENTS 4,733,130 A * 3/1988 Miyama et al. ............. 313/619
5,028,133 A    7/1991 Chevrier et al.
5,184,016 A * 2/1993 Ronan et al. ............... 250/288

FOREIGN PATENT DOCUMENTS

EP       0 437 358 A2    7/1991
JP       10221255        8/1998

OTHER PUBLICATIONS

"An Overview of GD–OES," by R. Payling, Glow Discharge Optical Emission Spectrometry, Edited by R. Payling, et al. 1997, John Wiley & Son, Ltd.

"Material Analysis Using the Emission Spectrometry," by Y. Lang, et al., I. Analysis of Liquid Samples by ICP; II Analysis by Spark Emission; III . Glow Discharge Optical Emission Spectrometry, Horiba Technical Reports, No. 16, Apr. 1998.

* cited by examiner

Primary Examiner—Zandra V. Smith

(57) ABSTRACT

This invention provides a glow discharge emission spectroscopic analysis apparatus which is capable of making a desired chemical analysis with excellent reproducibility. A glow discharge emission spectroscopic analysis apparatus of this invention is constituted so that the sample is held by a first electrical conductor provided on one side of a glow discharge tube and a second electrical conductor is movable by a cylinder rod to secure the sample in contact with the first electrical conductor. The electrical conductors can be electrically connected with each other when the sample is secured, and a negative electric potential is applied to the electrical conductors.

24 Claims, 7 Drawing Sheets

(A)

(B)

(C)

US 6,643,013 B1

GLOW DISCHARGE EMISSION SPECTROSCOPIC ANALYSIS APPARATUS

BACKGROUND OF THE INVENTION

1. Field of the Invention

The present invention relates to a glow discharge emission spectroscopic analysis apparatus, wherein a sample is arranged so as to face an anode of a glow discharge tube, an inert gas is supplied to the sample surface under low pressure and a glow discharge is emitted by applying a high-frequency voltage or a DC voltage between the sample and the anode so that a discharge emission can be analyzed and more specifically to an improvement in mounting and applying a potential voltage to a sample, such as a large semiconductor wafer.

2. Description of Related Art

One example of a glow discharge emission spectroscopic analysis apparatus is a high-frequency glow discharge emission spectroscopic analysis apparatus which can be utilized for chemical analysis of conductor, non-conductor and a semiconductor materials. With such an apparatus, sputtering and atomic emissions are combined for analyzing bulk solids and depth profiling surfaces and coatings.

According to recent developments in semiconductor techniques, the diameter of a semiconductor wafers such as silicon wafers used in manufacturing semiconductor circuit chips have become larger and the spacing between circuit paths have decreased so that minute impurities can impair the production of such products.

Thus, the prior art is seeking to find apparatus and procedures to precisely measure the properties of large semiconductor wafers.

SUMMARY OF THE INVENTION

The present invention provides a glow discharge emission spectroscopic analysis apparatus which is capable of making a desired chemical analysis with excellent reproducibility.

In order to achieve the above object, according to the present invention, in a glow discharge emission spectroscopic analysis apparatus where a sample is arranged so as to face an anode of a glow discharge tube provided in a Faraday cage, and an inert gas is supplied to the sample surface under a low pressure, and a glow discharge is emitted by applying a high-frequency voltage or a DC voltage between the sample and anode so that the discharge emission can be analyzed, the sample is maintained at the same potential as that of a negative electrode of the high frequency voltage or DC voltage provided on one of a front surface and a back surface of the sample excluding the sputtered position.

In the glow discharge emission spectroscopic analysis apparatus having the above structure, a voltage is applied to the sample uniformly, and intensity of the discharge emission becomes stable, and thus desired and stable analyzed results can be obtained.

In one embodiment, the sample can be held by a first electrical conductor provided on one side of the glow discharge tube and second electrical conductor which is capable of being close to or separated from the first electrical conductor, and both the electrical conductors are electrically connected with each other when the sample is mounted so that a negative electric potential is provided to both of the electrical conductors.

In the glow discharge emission spectroscopic analysis apparatus having the above structure, the sample is sandwiched between the first electrical conductor and the second electrical conductors. As a result, a voltage is applied to the sample uniformly, and the intensity of the discharge emission becomes stable, and thus desired and stable analyzed results can be obtained.

Further, in the glow discharge emission spectroscopic analysis apparatus, the first electrical conductor is provided to one end of the glow discharge tube, whereas the second electrical conductor is movable by a cylinder rod so that the sample can be held between both the electrical conductors. As a result, the sample can be held simply and securely in a predetermined posture.

The present invention can be provided to measure the properties of semiconductor wafers of a large size and the first and second electrical conductors can be designed to carefully hold the semiconductor wafer without exerting undue stress, while also providing a uniform application of voltage to both sides of the semiconductor wafer. An electrical conducting wiper can be provided to interconnect the first and second electrical conductors when they are closed on the semiconductor wafer for positioning the semiconductor wafer in a sealing relationship as a cathode in the glow discharge apparatus.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide a glow discharge emission spectroscopic analysis apparatus for measuring the properties of samples, such as semiconductor wafers.

The inventors of the present invention conceived of using a glow discharge emission spectroscope analysis to large size semiconductor wafers in a production environment and initially arranged for a sample of a semiconductor wafer to face an anode of a glow discharge tube. An inert gas was applied to the sample surface under a low pressure and a glow discharge was emitted by applying a high-frequency voltage between semiconductor wafer and the anode so as to analyze the discharge emission. However, scattering of analyzed data between a center portion and an outer peripheral portion of the semiconductor wafer surface surpassed the expected estimate of the inventors to create a problem. Moreover, scattering of the analyzed data according to various forms of other semiconductor wafers was also found to surpass the expected result, thereby indicating that the glow discharge analysis may not be dependable.

Figure 7:
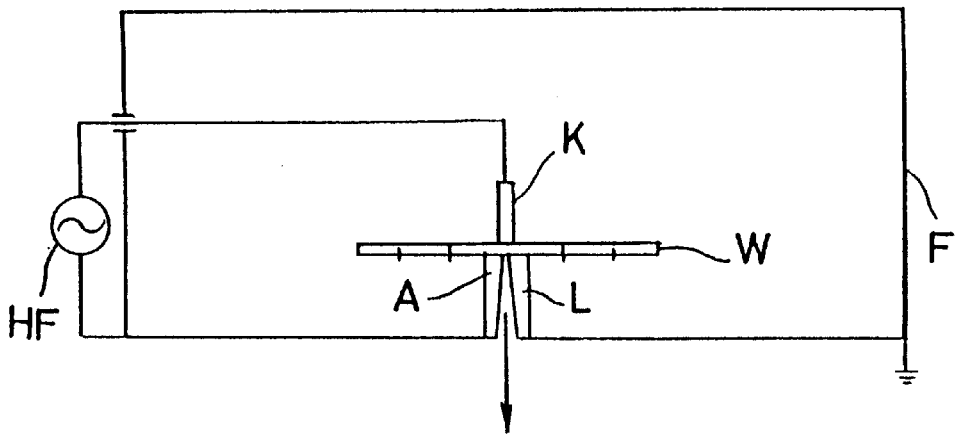
FIGS. 7A, 7B, and 7C are schematic drawings for explaining the problem found by the present inventors
Figure 7:
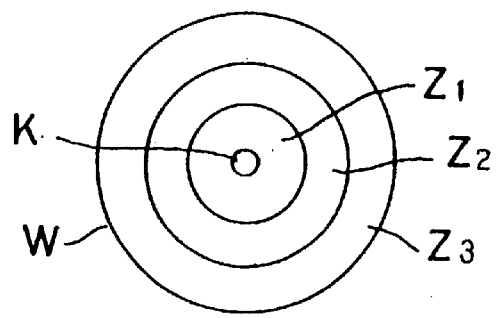
Figure 7:
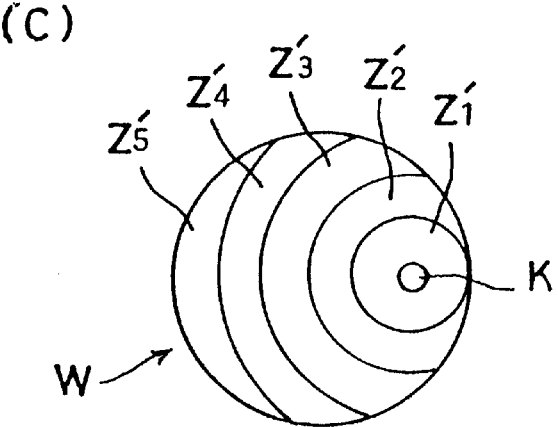

The inventors then examined their experimental results and came to a conclusion that the scattering was mainly caused by a state of coupling to a Faraday cage in portions other than the portion to which a high-frequency voltage was applied even if the same semiconductor wafer was used. This point will be described below with reference to FIG. 7.

FIG. 7(A) shows a state wherein a voltage is applied to a semiconductor wafer, and more specifically shows a semiconductor wafer W adjacent to an anode A side of a glow discharge tube L provided in a Faraday cage F so that the center of the semiconductor wafer W coincides with the center of the anode A. A cathode K is brought into contact with the semiconductor wafer W so as to coincide with the center of the semiconductor wafer W, and a high-frequency power source HF is connected between the anode A and the cathode K. FIG. 7(B) is a drawing showing a planar relationship between the semiconductor wafer W and the cathode K in the state of FIG. 7(A). Moreover, FIG. 7(C) is a drawing showing another planar relationship between the semiconductor wafer W and the cathode K, when K is off center.

As shown in FIG. 7(B), when the cathode K is brought into contact with the semiconductor wafer W so as to coincide with the center of the semiconductor wafer W, the semiconductor wafer W is composed of ring bands $Z_1$, $Z_2$ and $Z_3$, and the impedances of the ring bands are respectively $Z_1$, $Z_2$ and $Z_3$. In this case, the impedance $Z_t$ viewed from the cathode K is represented by the following equation (1).

$$Z_t = Z_1, Z_2 \text{ and } Z_3 \quad (1)$$

In addition, as shown in FIG. 7(C), when the cathode K is brought into contact with a peripheral portion of the semiconductor wafer W, the semiconductor wafer W is composed of ring bands $Z_1'$, $Z_2'Z_3'$, $Z_4'$ and $Z_5'$. In this case, the impedance $Z_t'$ viewed from the cathode K is represented by the following equation (2).

$$Z_t' = Z_1' + Z_2' + Z_3' + Z_4' + Z_5' \quad (2)$$

The impedance $Z_t$ of an arbitrary ring band is represented by the following equation (3).

$$Z_i = a_i + 1/jb_i \quad (3)$$

Here, $a_i$ is a resistance component for generating a voltage due to an electric current in an emission direction in the ring band, and $1/jb_i$ is a value relating to a capacitance coupling with the Faraday cage F of the ring band. In general, the impedance of the semiconductor wafer W is represented by $\Sigma Z_1$.

According to the above equations (1) through (3), it is clear that the $Z_t$ is different from $Z_t'$, and even if equal electric power is supplied to the semiconductor wafer W via the cathode K, the intensity of the discharge emission generated at this time varies, and thus analyzed results are different from each other.

The operation of a spectroscope, such as polychromator and monochromator systems, are known, see Glow Discharge Optical Emission Spectrometry by Payling et al., pages 20–23, pages 130–137, Wiley & Sons, Ltd. 1997.

The inventors consider that the above-mentioned problem is caused not only in the semiconductor wafer but also in a conductor, non-conductor and the like.

Figure 1:
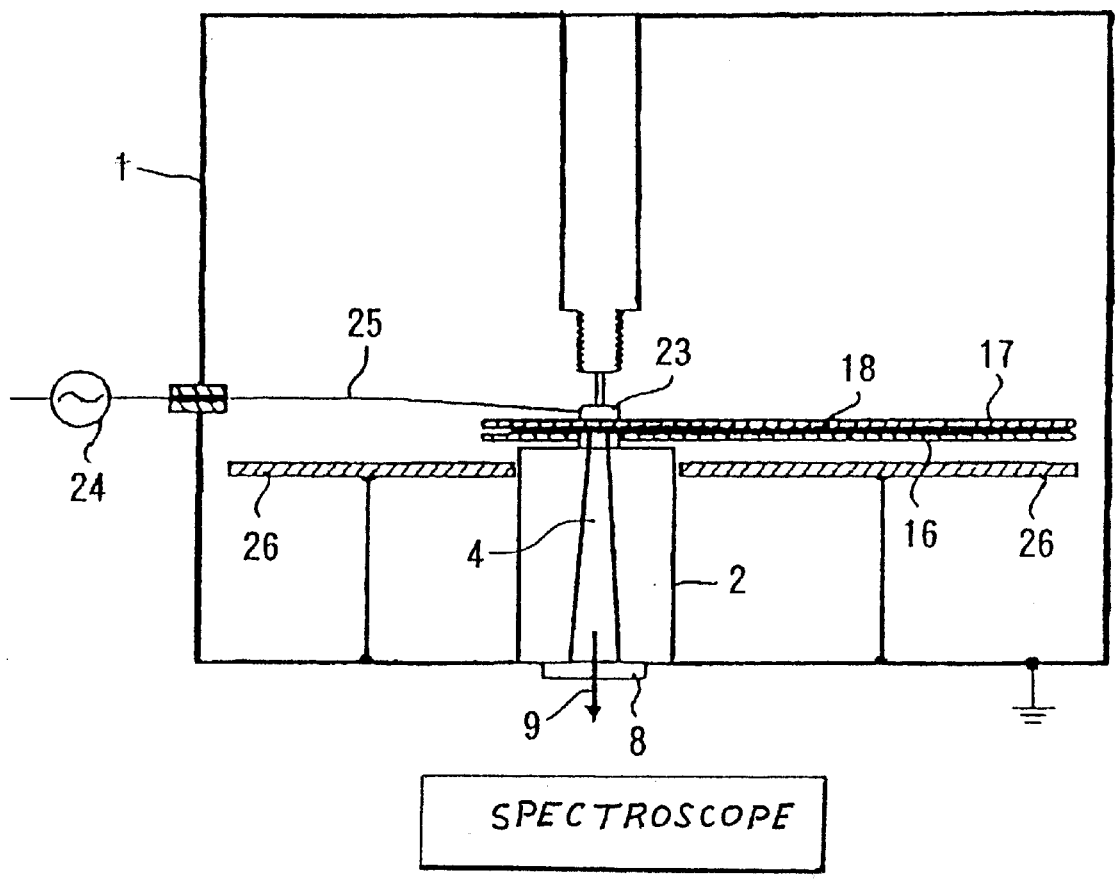
FIG. 1 is a drawing schematically showing a schematic structure of a glow discharge emission spectroscopic analysis apparatus of the present invention related to a first embodiment.
Figure 2:
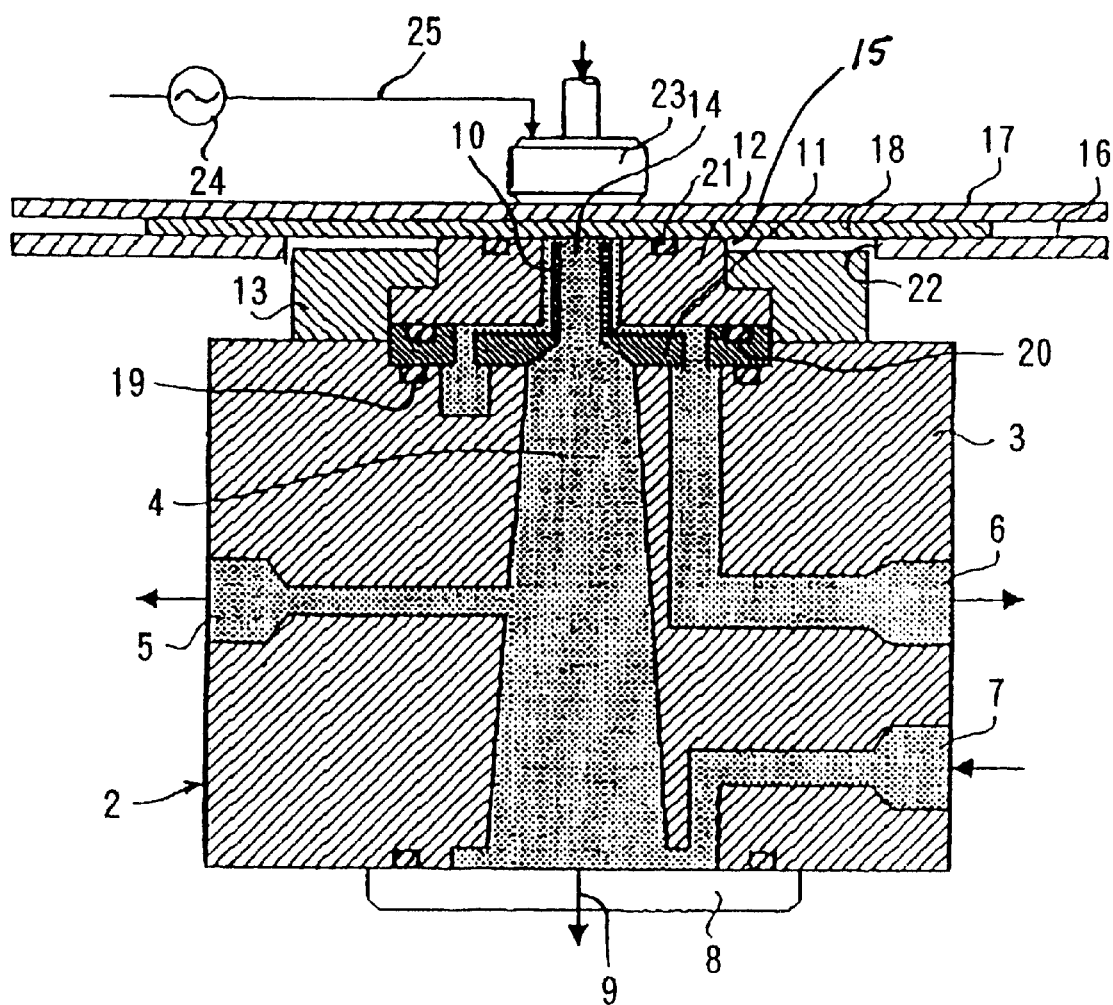
FIG. 2 is a cross-sectional view showing a main section of the above glow discharge emission spectroscopic analysis apparatus.

FIGS. 1 and 2 show a first embodiment of the present invention to resolve the above problem. At first, in FIG. 1, 1 is a metallic Faraday cage, and a glow discharge tube 2 is provided in the Faraday cage 1. There will be described below the structure of the glow discharge tube 2 and its periphery with reference to FIG. 2. 3 is a lamp body, and a discharge emission chamber 4 which broadens towards it bottom opening is formed therein. Vacuum ports 5 and 6 are formed in the lamp body 3, and they are connected with a vacuum pump, not shown. Moreover, 7 is a port for introducing an inert gas, appropriate for a sputtering plasma, such as argon gas.

An end on the broaden opening side of the discharge emission chamber 4 is sealed by a window 8 made of magnesium fluoride or the like, and light 9 which is generated due to a discharge, to be mentioned later, is introduced in a direction of a spectroscope. Moreover, an anode 11 having a cylindrical open portion 10 at its center is attached to the other end of the lamp body 3 which faces the window 8 by an anode holder 12 and a supporting body 13 made of, for example, ceramics so as to render airtight the lamp body 3. A through hole 14 into which the cylinder section 10 is inserted is formed in the anode holder 12, and a cylinder section 15 where the through hole 14 is formed is slightly projected from an upper surface of the supporting body 13 so that its peripheral portion is held by the supporting body 13. As mentioned above, the discharge emission chamber 4 on the anode 11 side is opened, but this opening is sealed by a surface of the semiconductor wafer 18 to be sputtered. As will be described later, the two conductors 16, 17 can mount and hold the wafer 18. Here, 19, 20 and 21 are sealing members, such as O-rings.

The conductors 16, 17, comprising copper plates of proper thickness, are conductors (hereinafter first conductor 16 and second conductor 17) for grasping the semiconductors wafer 18 and have an outer size larger than the semiconductor wafer 18. The first conductor 16 which is closer to the anode 11 has a hole 22 into which the anode holder or pressing member 12 can fit. As can be determined later, the first conductor 16 can be connected electrically with a second conductor 17 so that they become mutually the same in electrical potential.

Reference number 23 is a pressing member such as piston block or the like, which presses the rear face of the second conductor 17 when it cooperates with the first conductor 16 and grasps the semiconductor wafer 18. The pressing member 23 is connected with a negative pole if a high frequency power 24 is provided externally of the Faraday cage 1 through a conductor 25.

Referring to FIG. 1, reference numeral 26 is, for example, a plane copper plate which acts as an earth conductor when positioned close to the semiconductor wafer 18 and is also positioned so as to be parallel to it.

In order to conduct a material analysis of the semiconductor wafer 18 by using the glow discharge emission spectroscopic analysis apparatus, the wafer 18 is grasped by the two conductors 16 and 17 as shown in FIG. 1 and FIG. 2. The semiconductor wafer 18 is positioned to face the anode of the glow discharge tube 2, by pressing the second conductor 17 in the glow discharge tube 2 direction with the pressing member 23.

When a negative voltage is applied from a high-frequency power source 24 to the pressing member 23 in a state that the discharge emission chamber 4 provided in the glow discharge tube 2 is in an atmosphere of argon gas, a predetermined voltage is applied to the entire face of the semiconductor wafer 18 via the first electrical conductor 16 and the second electrical conductor 17. As a result, a discharge is generated, and argon ions are created based on the discharge, and the argon ions are accelerated by a high electric field so as to collide against the surface of the semiconductor wafer 18 which is the cathode, and is thereby subject to a predetermined sputtering process. The sputtered particles (atom, molecule and ion) are excited in the plasma, and when the particles return to a ground state, a light emission which is peculiar to the particular elements in the wafer is executed. This emitted light is introduced in the direction of the spectroscope as a light represented by a reference numeral 9 in FIG. 1 and FIG. 2.

In the glow discharge emission spectroscopic analysis apparatus, since the semiconductor wafer 18 as the sample to be analyzed is held by the first electrical conductor 16 and the second electrical conductor 17, the semiconductor wafer 18 can be held securely in a predetermined state. In the held state, the first electrical conductor 16 and the second electrical conductor 17 have equal or almost equal voltages, and both the electrical conductors 16 and 17 come close to the entire surface of the semiconductor wafer 18 on both faces. As a result, only by applying a high-frequency voltage to the first electrical conductor 16, a predetermined voltage can be applied to the whole surface of the semiconductor wafer 18, and the applying of a voltage to the semiconductor wafer 18 can be executed very simply and stably.

When the semiconductor wafer 18 was analyzed by using a glow discharge emission spectroscopic analysis apparatus, intensity of specified silicon wavelengths of 251 nm (secondary light), 288 nm (primary light) and 288 nm (secondary light) were examined. The results shown in the following TABLE 1 were obtained. In this measurement, a frequency of the high-frequency voltage was 13.56 MHz, an electric power was 50W, and a pressure in the glow discharge tube 2 was maintained within 4 to 5 mhPa.

Changing parameters are:
a. size of the semiconductor wafer 18 (6 in or 8 in);
b. position of the semiconductor wafer 18;
c. existence/non-existence of the two electrical conductors 16 and 17; and
d. distance from the semiconductor 18 to the earth conductor 26.

TABLE 1

| | 251 (2nd) | 288 (1st) | 288 (2nd) | Size (inch) | Position | Existence/ non-existence of electrical conductors | Distance (cm) |
|---|---|---|---|---|---|---|---|
| 1 | 806 | 800 | 33 | 6 | Center | Non-exist | 21 |
| 2 | 578 | 570 | 28 | 8 | Center | Non-exist | 21 |
| 3 | 234 | 232 | 11 | 8 | Edge | No-exist | 21 |
| 4 | 1152 | 1130 | 45 | 8 | Center | Exist | 21 |
| 5 | 1168 | 1157 | 46 | 8 | Edge | Exist | 21 |

TABLE 1-continued

| | 251 (2nd) | 288 (1st) | 288 (2nd) | Size (inch) | Position | Existence/ non-existence of electrical conductors | Distance (cm) |
|---|---|---|---|---|---|---|---|
| 6 | 1154 | 1152 | 46 | 6 | Edge | Exist | 21 |
| 7 | 1089 | 1070 | 42 | 8 | Edge | Exist | 11 |
| 8 | 851 | 835 | 33 | 8 | Edge | Exist | 5 |

The following is understood from TABLE 1. At first, in measurement 1 through measurement 3, a voltage was applied to the semiconductor wafer 18 as shown in FIG. 7(A) without using the first electrical conductor 16 and the second electrical conductor 17. In measurement 1 and 2, only the size of the semiconductor wafer 18 differed from each other, and as the size of the semiconductor wafer 18 was smaller, the emission intensity was stronger.

In measurement 2 and measurement 3, the sizes of the semiconductor wafer 18 were equal to each other, but the center of the semiconductor wafer 18 was measured in measurement 2, and a portion close to the edge of the semiconductor wafer 18 was measured in measurement 3. The emission intensity was stronger in the center of the semiconductor wafer 18.

Next, in measurement 4 through measurement 8, the semiconductor wafer 18 was sandwiched between the first electrical conductor 16 and the second electrical conductor 17 and in this state a voltage was applied to the semiconductor wafer 18. Measurement 4 and measurement 5 are different from each other only in that the measuring position of the semiconductor wafer 18 is its center or edge, and the other conditions were not different from each other. A difference in the intensity between respective wavelengths was hardly recognized.

In measurement 5 and measurement 6, the centers of the semiconductor wafers 18 with different sizes were measured, and the other conditions were not different from each other. A difference in the intensity between respective wavelengths was also hardly recognized.

In measurement 5, 7 and 8, the distances from the semiconductor wafer 18 to the earth conductor 26 differed from each other. Even if the first electrical conductor 17 held the semiconductor wafer 18 so as to cover it, as the distance between the semiconductor wafer 18 and the earth conductor 26 becomes shorter, the emission intensity is reduced. It is considered that this result occurs because the earth condition of the earth conductor 26 is incomplete at a high frequency and an electric power loss occurs, and thus the loss depends on the distance between the earth conductor 26 and the semiconductor wafer 18 so that the emission intensity changes. Moreover, it is also considered that when capacitive coupling between the first electrical conductor 16 and the second electrical conductor 17 and the earth conductor 26 exceeds a fixed amount, an energy for emission is reduced.

Although the same measurement was conducted in a condition where a conductor was adhered on either face of the semiconductor wafer 18 continuous to the above described measurement, no difference was recognized between the measurement results in either case. Namely, when the first conductor 16 is adhered only on the sputter face side of the semiconductor 18, and when the reverse face of the semiconductor wafer 18 is covered with the conductor 17 in a condition that the sputtered front face is exposed the same result is obtained as when the semiconductor wafer 18 is covered with the two conductors 16 and 17. Namely, when one front face of the semiconductor wafer 18 is retained at the same potential, the load is almost retained constant and it is not affected by the size of the semiconductor wafer 18 and the location of the voltage application.

Figure 3:
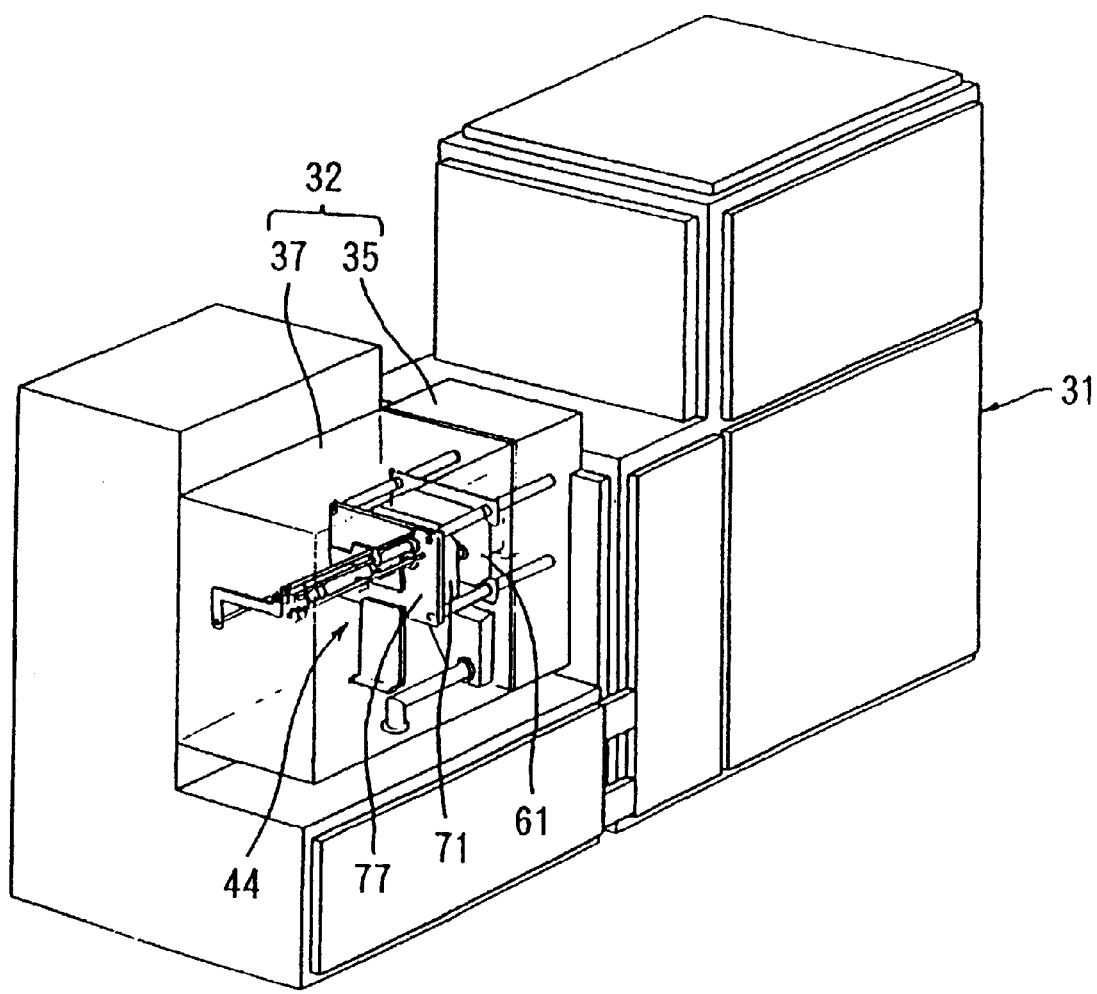
FIG. 3 is a perspective schematic view showing a the structure of a glow discharge emission spectroscopic analysis apparatus of the present invention related to the second embodiment for measuring semiconductor wafers, and more specifically a perspective view showing a Faraday cage.

There will be described below a second embodiment of this invention with reference to FIGS. 3 through 6. At first, in FIG. 3, 31 is an apparatus main body containing a spectroscope, such as a polychrometer and monochrometer for analyzing a discharge emission generated in a glow discharge tube (mentioned later), and a power source section and the like. This structure has been designed to accommodate thin flat discs, such as semiconductor wafers. A Faraday cage 32 is provided on the front side of the apparatus main body 31.

Figure 4:
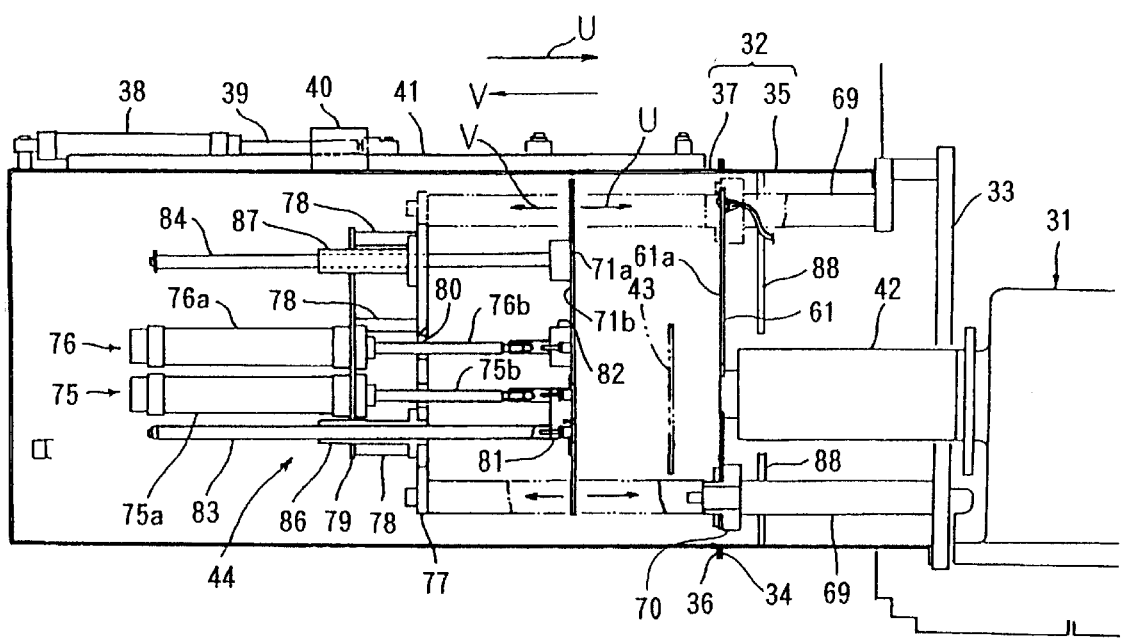
FIG. 4 is a cross-sectional schematic view showing a structure of a Faraday cage and the movable electrical conducting and holding members.

As shown in FIG. 4, the Faraday cage 32 is made of a metallic cylinder fixed to a bracket member 33 connected with the apparatus main body 31. The Faraday cage 32 is composed of a cylindrical first cage section 35 which is provided with a flange 34 and is made of metal, and a second cage section 37, which is provided so as to contact with or be separate from the first cage section 35, has a flange 36 at its one end, and is made of a metallic cylinder in which the other end is closed. 38 is an air cylinder whose one end is fixed to a side surface of the closed side of the second cage section 37, and a forward end of a piston rod 39 is coupled to a stanchion 40 which stands in a vertical direction in FIG. 4. The second cage section 37 slides in the direction of an arrow U or V by expansion and contraction of the piston rod 39 so that the flange 23 of the first cage section 35 and the flange 36 of the second cage section 37 closely contact with each other or are separated from each other by a predetermined gap. Here, 41 is a guide member. Accordingly, the housing structure of components 37 and 36 can be opened and closed to provide access for loading semiconductor wafers.

In the Faraday cage 32, a glow discharge tube 42, and a sample holding mechanism 44, which holds a sample 43 to be analyzed (for example, semiconductor wafer) to one end of the glow discharge tube 42 and applies a predetermined voltage to the sample 43, are provided.

Figure 5:
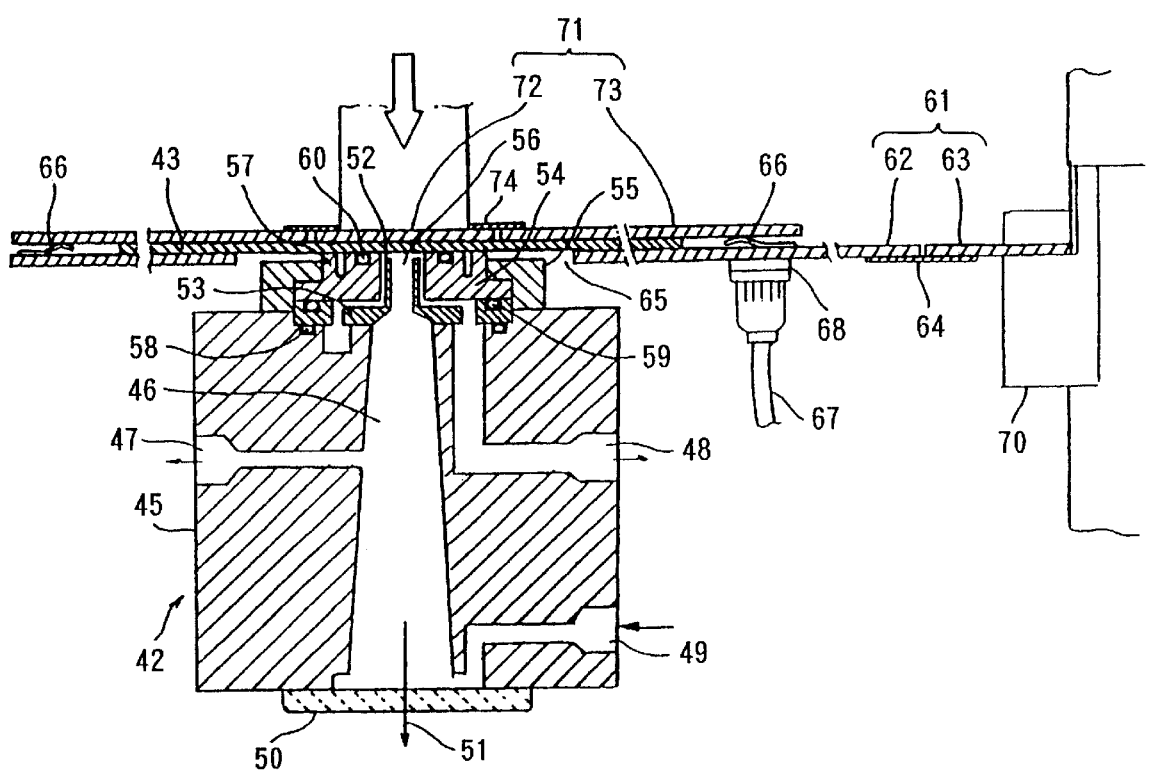
FIG. 5 is a sectional view showing a structure of a vicinity of a glow discharge tube related to a second embodiment of the present invention.

At first, a description will be given as to the structure of the glow discharge tube 42. In FIG. 5, 45 is a lamp body, and a discharge emission chamber 46 which broadens towards its bottom opening is formed therein. Vacuum ports 47 and 48 are formed in the lamp body 45, and they are connected with a vacuum pump, not shown. Moreover, 49 is a port for introducing an inert gas such as argon gas.

One end, on the broaden opening side of the discharge emission chamber 46, is sealed by a window 50 made of magnesium fluoride or the like, and any light 51 generated due to a discharge effect, mentioned later, is introduced in the direction of a spectroscope (not shown) in the apparatus main body 31. Moreover, an anode 53 having a cylindrical portion 52 at its center is attached to the other end which faces the window 50 by an anode holder 54 and a supporting body 55 made of, for example, ceramics so as to make airtight the lamp body 45. A through hole 56 into which the cylinder section 57, where the through hole 56 is formed, is slightly projected from an upper surface of the supporting body 55 so that its peripheral portion is held by the supporting body 55. As mentioned above, the discharge emission chamber 46 on the anode 53 is opened, but this opening is sealed by a surface of the semiconductor wafer 43 to be sputtered and held by the sample holding mechanism 44, mentioned later. Here 58, 59 and 60 are sealing members, such as O-rings.

Figure 6:
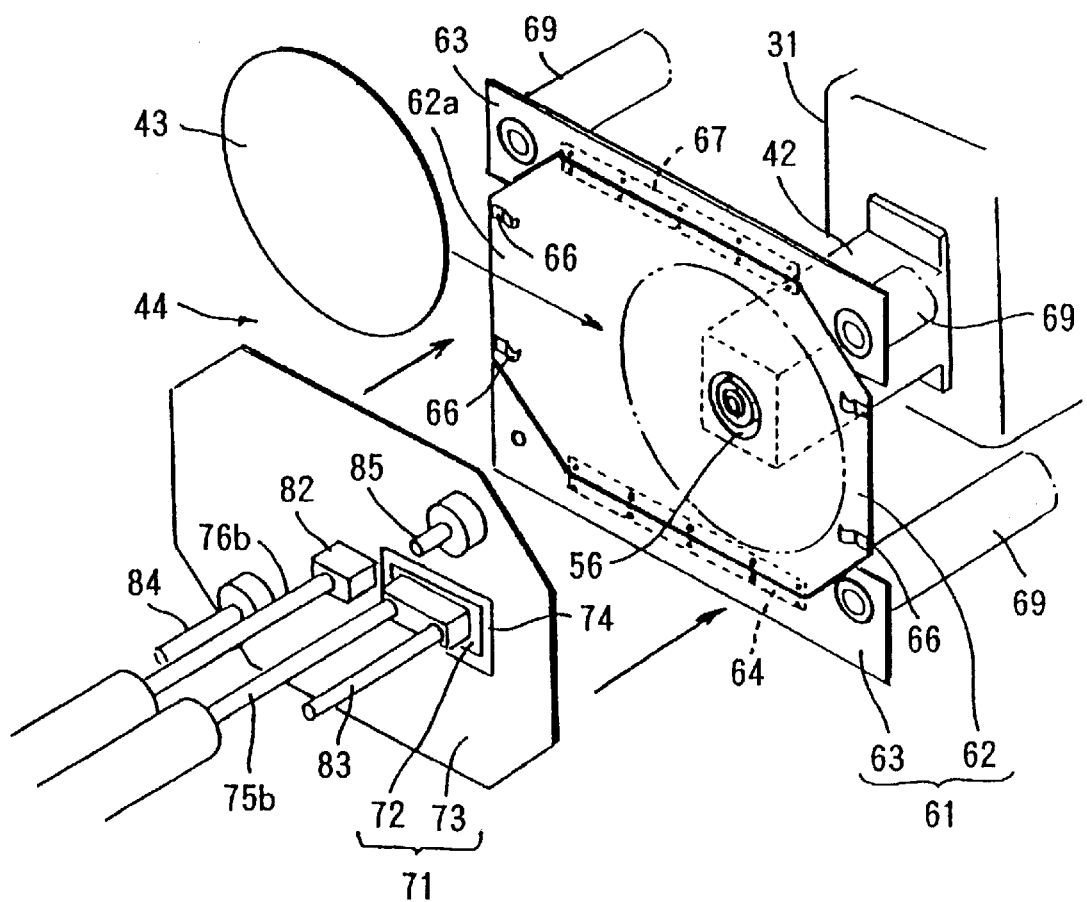
FIG. 6 is an enlarged perspective view showing a main section of a mechanism for holding a sample for the glow discharge tube in the second embodiment.

There will be described below the structure of the mechanism 44 for holding the semiconductor wafer 43 in a predetermined site also with reference to FIG. 6. The sample holding mechanism 44 is provided to the anode 53 side of the glow discharge tube 42. First, 61 is a first electrical conductor provided fixedly to the discharge tube 42, and it will sandwich the semiconductor wafer 43 with the cooperation on a second electrical conductor 71, mentioned later, so as to cover its whole surface, and it can apply a predetermined voltage to the semiconductor wafer 43. The first electrical conductor 61 as well as the second electrical conductor 71 will serve as a cathode for the discharge tube 42. The first electrical conductor 61 is made of a copper plate having a thickness of about 3 mm, for example, and is composed of a rectangular main body section 62 whose four corners are chamfered and two mounting sections 63. The main body section 62 and the mounting sections 63 whose size is at least larger than a maximum size of the semiconductor wafer 43 are coupled to each other by an elastic connecting plate 64 so that their rear faces (glow discharge tube 42 side) are flush with each other (there is no stepped portion) and will have an elastic structure to accommodate variances in the dimensions of the wafer 43.

A hole 65 which can house the supporting body 55 on the glow discharge tube 42 side is formed in the main body section 62, and an elastic and electrically conductive section 66, such as a wiper member, is provided for setting the voltages of the second electrical conductor 71 and the first electrical conductor 61 to be equal with each other. The wiper member 66 is projected from a suitable position of one side surface (surface opposite to the second electrical conductor 71, sandwich surface) 62a of the main body section 62, and a voltage apply section 68, connected with the high-frequency power source (not shown) via a cable 67, is provided on the other side surface.

In addition, the mounting sections 63 are held by insulating holding sections 70 (see FIG. 4) provided in midways of stanchions 69 which are held to the bracket member 33 (see FIG. 4) in a horizontal direction, and thus the first electrical conductor 61 is fixedly provided to the anode 53 of the glow discharge tube 42 so that its plane, particularly a sandwich surface represented by a reference symbol 62a (see FIGS. 4 and 6) is parallel with a vertical direction.

Here, the edge portions of the main body section 62 and the mounting sections 63 are subject to a curve face process and chamfering process so that an edge portion, which could score the wafer 43, is not generated.

71 is the second electrical conductor which is made of a copper plate of about 3 mm, for example, and it is provided so as to move linearly with respect to the fixed first electrical conductor 61. The second electrical conductor 71 has the same form and size as those of the main body section 62 of the first electrical conductor 61, but as shown in FIG. 5, it is composed of a small rectangular pressurizing section 72 which matches with the through hole 56 of the anode holder 54 (an area of the semiconductor wafer 43 to be analyzed is positioned here), and a main body section 73 of the pressurizing section 72. The pressurizing section 72 is coupled to the main body section 73 by an elastic coupling plate 74 so that they are flush with each other (a stepped portion is not generated). Here, the edge portion of the main body section 73 undergoes the curved face process and chamfering process so that an edge portion is not generated.

There will be described below holding and moving mechanisms of the second electrical conductor 71 with reference to FIGS. 4 and 6. In these drawings, 75 and 76 are air cylinders for moving the second electrical conductor 71 linearly, and their cylinder sections 75a and 76a are mounted to a mounting base 79 via spacers 78 which are held to a base member 77 mounted on the stanchions 69. Moreover, their piston rods 75b and 76b are constituted so as to be capable of expanding and contracting on the first electrical conductor 61 side through holes 80 opened in the base member 77. The ends of the piston rods 75b and 76b are mechanically coupled to connection blocks 81 and 82 provided on a side 71b (mounted face side) of the second electrical conductor 71 opposite to a surface 71a (see FIG. 4) for nipping or holding the pressurizing section 72 and the main body section 73.

83, 84, and 85 are guide rods provided in the same direction as a direction where the air cylinders 75 and 76 are provided laterally. As for the guide rod 83, its base portion is fixed to the connection block 81, which matches for the pressurizing section 72 of the second electrical conductor 71, and is inserted through a guide section 86 provided to the mounting base 79. As for the other two guide rods 84 and 85, their base portions are fixed to the main body section 72 of the second electrical conductor 71, and are inserted through a guide section 87 and a guide section, not shown, provided to the mounting base 79.

As mentioned above, the second electrical conductor 71 is held by the piston rods 75b and 76b of the two air cylinders 75 and 76 and the three guide rods 83 through 85 so as to be close to or separated from the first electrical conductor 61, and the contacting face 71a shield so as to be parallel with the contact face 62a of the first electrical conductor 61. Moreover, the second electrical conductor 71 holds the semiconductor wafer 43 in a vertical state by cooperation with the first electrical conductor 71.

Here, in FIG. 4, a plate-shaped earth conductor 88 is provided in the Faraday cage 32, and its voltage is maintained so as to be equal with the voltage of the Faraday cage 32.

In the case where the material of the semiconductor wafer 43 is to be analyzed by using the glow discharge emission spectroscopic analysis apparatus having the above structure, as shown in FIG. 4, the semiconductor wafer 43 to be analyzed is held between the electrical conductors 61 and 71 by a support loader or magic hand, not shown, in the state where the second electrical conductor 71 is separated from the first electrical conductor 61. When the two air cylinders 75 and 76 are operated, the piston rods 75b and 76b are extended in the direction of the arrow U. As a result, the semiconductor wafer 43 is pushed towards the direction of the first electrical conductor 61 so as to be nipped or securely held by the first electrical conductor 61 and the second electrical conductor 71. In this case, since the desired position of the semiconductor wafer 43 is previously known, the magic hand or loader positions the semiconductor wafer 43 so that the pressurizing section 72 in the second electrical conductor 71 matches with the through hole 56 where the anode 53 is provided.

As mentioned above, the semiconductor wafer 43 which is nipped by the first electrical conductor 61 and the second electrical conductor 71 is pressed against the anode holder 54 of the glow discharge tube 42, and since the sealing member 60 is provided on the pressed face side of the anode holder 54, the discharge emission chamber 46 of the glow discharge tube 42 is accordingly sealed by the surface of the semiconductor wafer 43 in an airtight manner. The area of the semiconductor wafer 43 to be analyzed (area to be sputtered) faces the cylinder section 52 of the anode 53 which is positioned in the through hole 56 of the anode holder 54.

In the above state, the main body section 73 of the second electrical conductor 71 contacts with the electrically conductive section 66 provided on the contact face 62a side of the main body section 62 of the first electrical conductor 61. Then, the voltage of the second electrical conductor 71 is made equal with the voltage of the first electrical conductor 61 so that the supporting contact area for the semiconductor wafer 43 is held at the same potential voltage.

When a high-frequency voltage is applied from a high-frequency power source (not shown) to the first electrical conductor 61 in a state that the discharge emission chamber 46 is in atmosphere of argon gas, a predetermined voltage is applied to the entire front and back face of the semiconductor wafer 43 via the first electrical conductor 61 and the second electrical conductor 71 which will have an equal voltage level. As a result, a discharge is generated, and an argon ion is created based on the discharge, and the argon ion is accelerated by a high electric field so as to collide against the surface of the semiconductor wafer 43 which acts as the cathode, and is thereby subject to a predetermined sputtering process. The sputtered particles (atom, molecule and ion) that are released from the semiconductor wafer 43 are then excited in the plasma field, and when the particles again return to a ground state, their characteristic wavelength emission is peculiar to the elements in the wafer 43. This emitted light is introduced in the direction of the spectroscope in the apparatus main body 31 as a light represented by a reference numeral 43 in FIG. 5.

As can be appreciated by determining the depth of etch or sputtering a profile as the elements in the wafer can be determined for not only the surface, but for controlled distances into the body of the wafer.

In the glow discharge emission spectroscopic analysis apparatus, since the semiconductor wafer 43 is nipped by the first electrical conductor 61 and the second electrical conductor 71, the semiconductor wafer 43 can be held securely in a predetermined state. In the nipped state, the first electrical conductor 61 and the second electrical conductor 71 have equal voltages, and both the electrical conductors 61 and 71 come close to each surface of the semiconductor wafer 43. As a result, only by applying a high-frequency voltage to the first electrical conductor 61, a predetermined voltage can be applied to the entire surface of the semiconductor wafer 43, and the applying of a voltage to the semiconductor wafer 43 can be executed very simply and stably. Particularly since a voltage from the high-frequency power source is applied to the fixed first electrical conductor 61, it is not necessary to install a power source cable, and thus installation of other components can be designed easily.

In addition, in the glow discharge emission spectroscopic analysis apparatus, the fixed first electrical conductor 61 is composed of the main body section 62 and the mounting sections 63, they are coupled with each other by the elastic coupling plate 64 so as to be flush with each other (no stepped portion is obtained), and thus the first electrical conductor 61 has an elastic structure. As a result, even if the semiconductor wafer 43 is slightly distorted or warped, the first electrical conductor 61 can absorb or adjust for the distortion and warpage, and can still hold the semiconductor wafer 43 in the desired position in cooperation with the second electrical conductor 71.

Furthermore, the movable second electrical conductor 71 is composed of the pressurizing section 72 for pressurizing the area of the semiconductor wafer 43 to be analyzed and the main body section 73, and has an elastic structure, and the pressing section 72 and the main body section 73 are pressurized respectively by individual piston rods 75b and 76b. As a result, when a pressurizing force of the piston rods 75b to the pressurizing section 72 is set to be larger than a pressurizing force of the piston rod 76b to the main body section 73, the portion of the semiconductor wafer 43 including the area to be analyzed can be pressed strongly against the anode holder 54, and thus a predetermined airtightness can be maintained.

Even when an analysis of the semiconductor wafer 43 was conducted by the use of the above described glow discharge emission spectroscopic analysis apparatus, the same result as that of the glow discharge emission spectroscopic analysis apparatus of the first embodiment has been obtained.

In the above embodiment, the second electrical conductor 71 is driven by the two air cylinders 75 and 76, but the present invention is not limited to this structure, and thus it may be driven by one air cylinder or by other hydraulic and electrical motive forces.

In addition, in the above embodiment, the semiconductor wafer 43 is used as a sample, but the present invention is not limited to this, and thus, conductors such as metal, non-conductors and semiconductors such as various insulating material including ceramics can be used for analysis. Further, when the sample is a conductor, it is needless to say that a DC voltage may be applied thereto instead of a high-frequency voltage.

Since the second embodiment of the glow discharge emission spectroscopic analysis apparatus is arranged so that the sample 43 is sandwiched between the first electrical conductor 61 s and the second electrical conductor 71 and a negative electric potential is given to one of them, a voltage is applied to the sample 43 uniformly, and the intensity of the discharge emission becomes stable. As a result, a desired and stable analyzed result can be obtained. Therefore, the desired chemical analysis may be made with excellent reproducibility.

It is not intended to limit this invention to the particular embodiments disclosed but, on the contrary, the invention is to cover all modifications and alternative constructions all within the spirit and scope of the invention as expressed in the appended claims and as known by those skilled in the field as equivalents to the elements set forth in the claims.

What is claimed is:

1. In a glow discharge spectrometer for generating a glow discharge by arranging a sample to face an anode of a glow discharge tube provided in a Faraday cage with inert gas adjacent a surface of the sample under low pressure condition and high frequency voltage or DC voltage applied between the sample and the anode, for analyzing the glow discharge generated, the glow discharge spectrometer improvement comprising:
    a first and second conductor member movably mounted to receive a sample therebetween;
    a force assembly for pressing the sample to seal against the glow discharge tube; and
    an electrical connector for providing a common electrical potential to the first and second conductors so that the sample acts as a cathode at a uniform potential.

2. The invention of claim 1, wherein one conductor member has an aperture to accommodate a portion of the sample that is to be analyzed.

3. The invention of claim 1, wherein the force member is a cylinder rod.

4. The invention of claim 1 wherein the force member is a pair of cylinder rods.

5. The invention of claim 1 wherein the electrical connector is a wiper member.

6. The invention of claim 1 wherein one of the conductor members is resiliently mounted to permit adjustable movement between the conductor member and the sample when the sample is mounted between the first and second conductor members.

7. The invention of claim 1 further including means for applying a pressurizing force to a surface of the sample opposite the anode for sealing the sample to the glow discharge tube.

8. A method of analyzing a semiconductor wafer, comprising the steps of:
    positioning a semiconductor wafer between a first and second conductor member, the first conductor has an aperture to expose a surface of the wafer and the second conductor has a corresponding section to the opposite aperture for exerting a sealing force;
    closing the first and second conductor to secure the semiconductor wafer;
    positioning the exposed surface of the semiconductor wafer to an opening in a glow discharge chamber;
    applying a force to seal the semiconductor wafer to the glow discharge chamber;
    providing a sputtering gas to the glow discharge chamber;
    applying an electrical potential to the semiconductor wafer through the first and second conductors to create a uniform negative potential of sufficient magnitude to cause a plasma of the sputtering gas to erode the semiconductor wafer; and
    analyzing the glow discharge emission of light to determine the elements in the semiconductor wafer.

9. The method of claim 8 further including resiliently mounting at least one of the first and second conductor members so that the semiconductor wafer is resiliently mounted upon closing of the first and second conductor member.

10. The method of claim 8 further including applying a negative high frequency voltage.

11. The method of claim 8 further closing the first and second conductors with air pressure.

12. An apparatus for determining the elements in a semiconductor wafer, comprising:
    a first conductor member having a central aperture and of a size larger than the wafer;
    a second conductor member of a size larger than the wafer;
    means for opening and closing the first and second conductor members to mount the wafer therebetween;
    a glow discharge chamber apparatus having an opening adjacent the central aperture of the first conductor member and an anode within the chamber;
    means for exerting a force on the wafer to seal the wafer to the glow discharge chamber apparatus opening when the wafer is mounted between the first and second conductors;
    means for providing a sputtering gas to the glow discharge chamber apparatus;
    means for providing an electrical charge between the first and second conductors to uniformly charge the wafer as a cathode to the anode whereby a glow discharge emission is created as the wafer is sputtered; and
    means for providing a spectroscopic analysis of the light from the glow discharge emission to determine the elements in the wafer.

13. An apparatus for determining the elements in a semiconductor wafer, comprising:
    a conductor member having an aperture, the conductor member has a size to extend across the semiconductor wafer to enable an application of uniform potential to be applied to a surface of the semiconductor wafer to be sampled;

means for mounting the semiconductor wafer on the conductor member;

a glow discharge chamber unit having an anode and an opening adjacent the aperture of the conductor member;

means for exerting a force on the semiconductor wafer including a pair of pressure rod members to seal at least a portion of the surface to be sampled to the glow discharge chamber unit opening when mounted on the conductor member;

means for providing a sputtering gas to the glow discharge chamber unit;

means for providing an electrical charge of sufficient power to the conductor member to uniformly charge the surface of the semiconductor wafer as a cathode to the anode, whereby a glow discharge emission is created as the semiconductor wafer is sputtered; and means for providing spectroscopic analysis of the light from the glow discharge emission to determine the elements in the semiconductor wafer.

14. The apparatus of claim 13 wherein the conductor member is larger in size than the semiconductor wafer.

15. The apparatus of claim 13 wherein the conductor member is resiliently mounted to permit adjustable movement between the conductor member and the semiconductor wafer when the semiconductor wafer is mounted on the conductor member.

16. The apparatus of claim 13 wherein one of the pressure rod members, aligned with the anode, exerts a greater force on the semiconductor wafer than the other pressure rod member.

17. A system for determining the elements in a semiconductor sample, comprising:

a semiconductor wafer;

a first conductor member, the first conductor member has a size to extend across the semiconductor wafer to enable an application of uniform potential to be applied to a first surface of the semiconductor wafer to be sampled;

a second conductor member for contacting the opposite side of the semiconductor wafer from the other conductor member;

means for mounting the semiconductor wafer on the first conductor member;

a glow discharge chamber unit having an anode and an opening adjacent the first conductor member;

means exerting a force on the semiconductor wafer to seal at least a portion of the surface to be sampled to the glow discharge chamber unit opening when mounted on the first conductor member;

means for providing sputtering gas to the glow discharge chamber unit;

means for providing an electrical charge of sufficient power to the first conductor member to uniformly charge the surface of the semiconductor wafer as a cathode to the anode, whereby a glow discharge emission is created as the semiconductor wafer is sputtered; and means for providing a spectroscopic analysis of the light from the glow discharge emission to determine the elements in the semiconductor wafer.

18. An apparatus for determining the elements in a semiconductor wafer, comprising:

a conductor member having an aperture, the conductor member has a size to extend across the semiconductor wafer to enable an application of uniform potential to be applied to a surface of the semiconductor wafer to be sampled;

means for mounting the semiconductor wafer on the conductor member;

a glow discharge chamber unit having an anode and an opening adjacent the aperture of the conductor member;

means for exerting a force on the semiconductor wafer to seal at least a portion of the surface to be sampled to the glow discharge chamber unit opening when mounted on the conductor member, including a pair of pressure rod members;

means for providing a sputtering gas to the glow discharge chamber unit;

means for providing an electrical charge of sufficient power to the conductor member to uniformly charge the surface of the semiconductor wafer as a cathode to the anode, whereby a glow discharge emission is created as the semiconductor wafer is sputtered; and means for providing a spectroscopic analysis of the light from the glow discharge emission to determine the elements in the semiconductor wafer.

19. The apparatus of claim 18 wherein the conductor member is larger in size than the semiconductor wafer.

20. The apparatus of claim 18 wherein the conductor member is resiliently mounted to permit adjustable movement between the conductor member and the semiconductor wafer when the semiconductor wafer is mounted on the conductor member.

21. The apparatus of claim 18 wherein one of the pressure rod members, aligned with the anode, exerts a greater force on the semiconductor wafer than the other pressure rod member.

22. A system for determining the elements in a semiconductor sample, comprising:

a semiconductor wafer, a first conductor member, the first conductor member has a size to extend across the semiconductor wafer to enable an application of uniform potential to be applied to a surface of the semiconductor wafer to be sampled;

a second conductor member for contacting the opposite side of the semiconductor wafer from the first conductor member;

means for mounting the semiconductor wafer between the first and second conductor members;

a glow discharge chamber unit having anode and a opening adjacent the first conductor member;

means for exerting a force on the semiconductor wafer to seal at least a portion of the surface to be sampled to the glow discharge chamber unit opening when mounted on the first conductor member;

means for providing a sputtering gas to the glow discharge chamber unit;

means for providing an electrical charge of sufficient power to the first conductor member to uniformly charge the surface of the semiconductor wafer as a cathode to the anode, whereby a glow discharge emission is created as the semiconductor wafer is sputtered; and means for providing a spectroscopic analysis of the light from the glow discharge emission to determine the elements in the semiconductor wafer.

23. The system of claim 22 wherein the first conductor member is larger in size than the semiconductor wafer.

24. A system for determining the elements in a semiconductor sample, comprising:

a semiconductor wafer a conductor member, the conductor member has a size to extend across the semiconductor wafer to enable an application of uniform potential to be applied to an entire surface of the semiconductor wafer to be sampled, the conductor member is larger in size than the semiconductor wafer;

means for mounting the semiconductor wafer on the conductor member;

a glow discharge chamber unit having an anode and an opening adjacent the conductor member;

means for exerting a force on the semiconductor wafer to seal at least a portion the surface to be sampled to the glow discharge chamber unit opening when mounted on the conductor member;

means for providing sputtering gas to the glow discharge chamber unit;

means for providing an electrical charge of sufficient power to the conductor member to uniformly charge the surface of the semiconductor wafer as a cathode to the anode, whereby a glow discharge emission is created as the semiconductor wafer is sputtered; and means for providing a spectroscopic analysis of the light from the glow discharge emission to determine the elements in the semiconductor wafer.

* * * * *